(12) United States Patent
Gomez

(10) Patent No.: US 8,287,702 B2
(45) Date of Patent: Oct. 16, 2012

(54) ELECTROLYTIC ACTIVATION OF WATER

(76) Inventor: Rodolfo Antonio M. Gomez, Brompton (AU)

( * ) Notice: Subject to any disclaimer, the term of this patent is extended or adjusted under 35 U.S.C. 154(b) by 716 days.

(21) Appl. No.: 12/284,158

(22) Filed: Sep. 17, 2008

(65) Prior Publication Data
US 2009/0071844 A1   Mar. 19, 2009

Related U.S. Application Data

(63) Continuation-in-part of application No. 12/074,385, filed on Mar. 3, 2008, now abandoned, which is a continuation of application No. 10/480,412, filed on Dec. 10, 2003, now abandoned, said application No. 12/284,158 is a continuation of application No. PCT/AU2007/000809, filed on Jun. 8, 2007.

(51) Int. Cl.
*C02F 1/46* (2006.01)

(52) U.S. Cl. ............ 204/272; 204/275.1; 205/701; 205/742

(58) Field of Classification Search .............. 205/701, 205/742; 204/242, 272, 275.1
See application file for complete search history.

(56) References Cited

U.S. PATENT DOCUMENTS

| | | | | |
|---|---|---|---|---|
| 3,770,612 A | * | 11/1973 | Gray et al. | 204/261 |
| 5,599,437 A | * | 2/1997 | Taylor et al. | 205/744 |
| 5,728,287 A | | 3/1998 | Hough et al. | |
| 5,882,502 A | * | 3/1999 | Gomez | 205/568 |

FOREIGN PATENT DOCUMENTS

WO   WO 88/03966   6/1998

\* cited by examiner

*Primary Examiner* — Arun S Phasge
(74) *Attorney, Agent, or Firm* — Klauber & Jackson LLC

(57) ABSTRACT

The commercial unipolar activation of water to disinfect raw water supply from rivers or wells, seawater, or waste water from sewage, animal waste, processing plant waste, cooling tower water, swimming pool and spa water, ship ballast water and similar polluted waters. Disinfection is accomplished by hydrogen peroxide and ozone including biocides from chlorine and sulphur compounds in the water that are produced during the electrolytic unipolar activation of the water. Unipolar activation can also be used to perform chemical reactions such as in the activation of seawater. This invention can also produce alkaline water that is beneficial for health.

6 Claims, 15 Drawing Sheets

ELECTROLYTIC ACTIVATION OF WATER

CROSS REFERENCE TO RELATED APPLICATIONS

The present application is a continuation in part of U.S. Ser. No. 12/074,385 filed on Mar. 3, 2008 now abandoned which is a continuation of U.S. Ser. No. 10/480,412 filed on Dec. 10, 2003 and having the benefit of international application PCT/AU02/00777 filed Jun. 14, 2002 now abandoned which in turn claims priority to Australian Patent Application PR 5667 filed on Jun. 14, 2001. The present application is also a continuation of international application PCT/AU2007/000809 filed on Jun. 8, 2007 which in turn claims priority to Australian Patent Application 2006903142 filed Jun. 9, 2006, Australian Patent Application 2006906436 filed Nov. 20, 2006 and Australian Patent Application 2007900552 filed Feb. 6, 2007.

FIELD OF INVENTION

This invention concerns an electrolytic process called unbalanced electrolysis or unipolar activation for the treatment of water.

INTRODUCTION

With increasing world population and the problems caused by climate change, water supply has become a major problem in many parts of the World. Until this invention, chlorination has been the major method of disinfection of water for human or agricultural use. Many studies have shown that hydrocarbon chlorides such as chloramines that are product of the chlorination process are carcinogenic. Other disinfection methods such as ultra-violet and ozone production and application to water supply have major limitations.

Unipolar activation for the treatment of water is a process where electrons are removed by the DC power source from a liquid passing through an anode cell and electrons are added to a separate liquid passing through a cathode cell, the process producing synthetic compounds. At the anode, strong biocides such as hydrogen peroxide can be produced while at the cathode, weaker compounds can be produced.

This invention utilises the diaphragm-less electrolytic cell described in my U.S. Pat. No. 5,882,502 (Mar. 16, 1999) and my Australian Patent 707701 (Oct. 28, 1999). This construction allows high capacity and efficiency compared to the conventional diaphragm cell of an earlier invention on unipolar activation. The unipolar activation of liquids was described in general in my United Kingdom Patent no. GB2392441 (21 Jul. 2004).

PRIOR ART

The activation of liquids by subjecting the liquid to unipolar activation or unbalanced electrolysis is becoming a major branch of chemistry. The subject has been studied extensively in Russia and the studies have been published by Dr. Vitold Bakhir in several papers. Dr. Bakhir, et al have been granted U.S. Pat. No. 5,427,667 (Jun. 27, 1995) for an apparatus for the electrochemical treatment of water, with the objective of sterilizing the water or using the product as a disinfectant. Dr. Bakhir's apparatus is tubular in shape and is diagrammatically shown in FIG. 1. The outer tube may be the anode electrode and the inner tube may be the cathode electrode. The electrodes are separated by a cylindrical ceramic diaphragm. Liquid is fed into the outer tube and is discharged as an anolyte and a separate liquid is fed into the inner tube and is discharged as a catholyte. There is no mixing of the liquids and the apparatus acts to remove electrons from the anolyte and add electrons to the catholyte. In subsequent papers, Dr. Bakhir indicated that unbalanced electrolysis was less efficient when there is no diaphragm between the anode and cathode electrodes.

While the major application of Dr. Bakhir's apparatus is the treatment of water, the application of unbalanced electrochemical activation is very extensive as described in the papers of Dr. Bakhir. The benefits of unipolar activation can be examined in almost every commercial application in energy, health, agriculture, environment, and general industries. The only limitation in most cases is the use of a diaphragm between the anode and cathode electrodes that limit reaction rates due to the impedance of the diaphragm and problems from blockage of the diaphragm from solids and salt formation.

I have been granted Australian Patents 654774 (Mar. 29, 1993), 707701 (Oct. 28, 1999) and U.S. Pat. Nos. 5,569,370 (Oct. 29, 1996), 5,882,502 (Mar. 16, 1999) regarding a unique electrolytic cell that does not use a diaphragm or membrane between the anode and the cathode electrodes. This electrolytic cell has a very high Faraday efficiency, a higher energy efficiency and faster reaction rate than conventional diaphragm cells allowing this electrolytic cell to be used in commercial applications particularly where the use of a diaphragm is a disadvantage because of blockage of the diaphragm from solid particles, deposits of salts or oily electrolytes.

The application to unipolar activation or unbalanced electrolysis is illustrated in FIG. 2. Electrons are removed from the liquid feed to the anode cell producing an acid anolyte with strong biocides. At the cathode cell, electrons are added into the separate liquid feed resulting in a catholyte that is alkaline with weak washing solutions. The production of acid water from the anode cell and alkaline water from the cathode cell was confirmed in tests in our large scale laboratory apparatus. Electrons travel from the anode electrode to the DC power source to the cathode electrode through the catholyte to the cathode solution electrode to the anode solution electrode through the anolyte to the anode electrode to form the complete electronic circuit of the unipolar electrolytic cell. The applicant has been granted United Kingdom patent no. GB2392441 (Jul. 21, 2004) titled "Electrolytic Activation of Fluids" where the unipolar activation of water using the apparatus shown on FIG. 2 was applied.

DESCRIPTION OF THE INVENTION

In one form, therefore, the invention comprises a unipolar electrolytic apparatus to activate water comprising an anode cell assembly and a cathode cell assembly, the anode cell assembly including an anode electrode and a solution electrode and the cathode cell assembly including a cathode electrode and a solution electrode, a power supply that provides a DC pulsed current to the anode cell assembly and the cathode cell assembly and the connections of the cathode solution electrode and the cathode electrode being interchanged to result in the cathode cell behaving like an anode cell in an anode mode, whereby oxidizing reactions occur in the water at both anode cell and cathode cell in the anode mode, such that strong biocides are produced in both the anode cell and the cathode cell, or the connections between the anode solution electrode and the anode electrode being interchanged to result in the anode cell behaving like the cathode cell in a cathode mode where reducing reactions occur in the water at both anode cell and cathode cell in the cathode mode.

Preferably the DC current applied has a pulse frequency of 20 to 200 kilohertz and the DC pulsing current can have a duty cycle of the range of from 20 to 80 percent.

The anode cell assembly and the cathode cell assembly can operate at a temperature of from 10 degrees Celsius to 200 degrees Celsius and at a pressure of from atmospheric pressure up to 300 psig (22 atm).

Preferably the anode electrode and the cathode electrode each comprise an expanded metal mesh and comprise or are coated with a material providing a low over-voltage and resistance to corrosion. Further, the anode electrode and the cathode electrode held between plate solution electrodes can include baffles of an electrically non-conductive material to force the water to weave in and out of the expanded metal electrode.

The anode cell and cathode cell solution electrodes can be of solid construction to guide the water to weave in and out of the expanded metal electrode.

In an alternative form the invention comprises a process of treating water using a unipolar electrolytic apparatus as discussed above wherein acid water is produced from both anode cell and cathode cell when the cathode cell is connected in the anode mode.

In an alternative form the invention comprises a process of treating water using a unipolar electrolytic apparatus as discussed above wherein alkaline water is produced from both anode cell and cathode cell when the anode cell is connected in the cathode mode.

In one embodiment the feed water is sea water or water containing alkali metals and the process of unipolar activation results in the production of hydrogen and an excess of hydroxyl ions leading to the formation of alkali hydroxides. The activated water can be contacted with carbon dioxide gas to sequester the carbon dioxide as an alkali metal carbonate or bicarbonate. Preferably modifiers are added to the water before or after activation to improve the absorption and sequestration of the carbon dioxide. The absorption of the carbon dioxide can be carried out at elevated temperature and pressure in a counter current system.

In an alternative form the invention comprises a method of sequestering carbon dioxide in water, the method comprising the steps of passing the water through a unipolar electrolytic apparatus as defined above acting in cathode mode to produce an activated water, and contacting the activated water with carbon dioxide in the water to produce alkali carbonates as a precipitate. The water can be sea water.

In an alternative form the invention comprises a method of disinfecting water, the method comprising the steps of passing the water through a unipolar electrolytic apparatus as defined above acting in anode mode to produce a disinfected water that is suitable for human use or for irrigation after filtration of precipitated solids. The water can be sewage water, raw water supply, or polluted water from industrial operations.

Hence it will be seen that this invention there is provided a water activation apparatus with one or more of the following characteristics:

1. Changing Cell Modes of Operation

A diaphragm cell can operate only with an anode electrode where oxidation reactions occur and a cathode electrode where reducing reactions occur. Experiments with our diaphragm-less unipolar system using a large scale unipolar apparatus have showed that by connecting the anode solution electrode to the cathode electrode and the cathode solution electrode to the negative of the DC power source, the cathode cell behaved like an anode cell. The pH of the catholyte from the cathode cell became acidic instead of alkaline as shown on FIG. 3 below. Looking at the current flow, electrons are being removed from the cathode electrode in a similar way to the anode electrode. Similarly, when the connections are changed as shown on FIG. 4 below, where the positive of the DC power source is connected to the anode solution electrode and the anode electrode connected to the cathode solution electrode, the anolyte became alkaline. The direction of the current flow to the anode electrode is the same as the current flow to the cathode electrode.

This is a very significant discovery because if the application of the unipolar activation of water is disinfection, all the energy applied to the water is applied to disinfection as compared to the conventional diaphragm cell where only half of the activated water has strong biocides. This discovery can also be used to perform chemical reactions in liquids such as the activation of seawater where hydrogen is produced leaving an excess of hydroxyl ions in the seawater.

2. Pulsing Frequency of the Electric Current

Disinfection is a major application of unipolar activation where the strong biocides hydrogen peroxide and ozone are produced at the anode cell. In the experiments, the hydrogen peroxide was measured by a Palintest Model 8000 calorimeter. The pulsing rate was varied from 0.005 kilohertz to 50 kilohertz. The results are shown on FIG. 5 below where production of hydrogen peroxide increased significantly with the increase of the pulsing frequency up to 50 kilohertz.

Field tests were carried out using a portable 200 liters per minute unipolar activation unit according to the present invention to disinfect sewage water at Westernport Sewage plant. FIG. 7 below shows the effect of the electrical energy input into the sewage water on the survival rate of pathogens. The total plate count was reduced from 240,000 counts per 100 ml to 500 counts per 100 ml for both the anode water and cathode water with the cathode in anode mode. The cell voltage was 20 volts with electrode gap of 6 millimeters.

The variation of the pathogen survival rate in FIG. 7 was within experimental error and it can be concluded that the biocide produced at the anode and at the cathode cells were about the same. This confirms the finding in the large scale laboratory tests that the cathode can be connected electrically so that it behaves like an anode cell.

3. Effect of Electrode Gap

Measurements have shown that the total voltage is equal to the sum of the voltage between the anode electrode and the anode solution electrode and, the voltage between the cathode electrode and the cathode solution electrode, providing the solution characteristics are about the same and the amperes per square meter are the same at the anode and at the cathode.

4. Effect of Pressure on Biocide Production

Test conducted on Feb. 14, 2007 on rainwater gave the following indication of the effect of pressure on the production of hydrogen peroxide and ozone—

|  | Duty | KHz | Volts | Amps | $H_2O_2$, mg/L | $O_3$, mg/L | Pres., psig |
|---|---|---|---|---|---|---|---|
| Test 11 | 60 | 50 | 36 | 10.2 | 2.1 | 4.0 | 0 |
| Test 14 | 60 | 50 | 36 | 10.2 | 2.1 | 4.2 | 0 |
| Test 15 | 60 | 50 | 34.3 | 10.2 | 4.5 | 6.8 | 17 |

The tests 14 and 15 were conducted with oxygen addition of 250 cc/min to the cell. This test shows pressure in the cell would improve the production of hydrogen peroxide and ozone but the addition of oxygen did not improve the production of hydrogen peroxide and ozone.

The tests on Pt. Elliot sewage water further showed the effect of pressure on the production of biocides as measured from the objective of reducing the E. coli count to zero, as follows:

| Test No. | Volts | Amps. | Pres., psig | E. coli/ 100 ml | Start E. coli/ 100 ml |
|---|---|---|---|---|---|
| PESW 5/24 | 24 | 11.6 | 0 | 1,300,000 | 2,400,000 (no aeration) |
| PESW 3-3 | 18 | 10 | 20 | 0 | 240,000 (after aeration) |
| PESW 3-4 | 20 | 12.5 | 20 | 0 | 240,000 (after aeration) |

The effect of pressure during activation for the production of biocides is very significant even at the low pressure levels.

5. Effect of Temperature

The effect of temperature in the production of biocides was not investigated because it is not economical to heat raw or sewage water before activation. However, in some applications, the water is warm or hot and in these applications, it is expected that the reaction rates will be faster and the voltage to achieve the reactions would be lower than when the water is cooler.

6. Electrode Construction

The anode and cathode electrodes may be constructed with a high unit surface area such as expanded metal. The sheared nature of the expanded metal not only create large surface area but the sheared surfaces contain a large number of active surfaces. The electrodes are coated with suitable material to reduce over-voltage and to protect against corrosion. A preferred construction is expanded titanium sheet and coated with platinum group oxides that has been used universally in these experiments.

The solution electrodes may be made of plain sheets of titanium coated with platinum group oxides or since the solution electrode where the cells are in anode mode are acting as "cathodes", stainless steel plate electrodes have been used successfully.

The type of metal used in the electrode could also influence the results of the activation of water. In the portable unit discussed above, using expanded iron electrodes in anode mode resulted in the removal of about 92% of the phosphates and about 45% of the nitrates in the sewage water. Trials are planned to use aluminum electrodes to remove chlorides in the sewage water with or without the addition of calcium ions.

In the electrode assembly, the anode or cathode electrodes are held between the plate solution electrodes and non-conductor baffles are installed so that the water weaves in and out of the expanded metal electrodes. This creates very good contact between the water and the anode or cathode electrodes.

7. Alkaline water can be produced from both anode and cathode cell when the anode cell is in cathode mode. There are many who believe that alkaline water is good for human and animal health.

DESCRIPTION OF THE DRAWINGS

This then generally describes the invention but to assist with understanding reference will now be made to the accompanying drawing which show the prior art and preferred embodiments and examples of application of the present invention to various water disinfection and carbon dioxide sequestration applications.

In the drawings.

DESCRIPTION OF PRIOR ART

Figure 1:
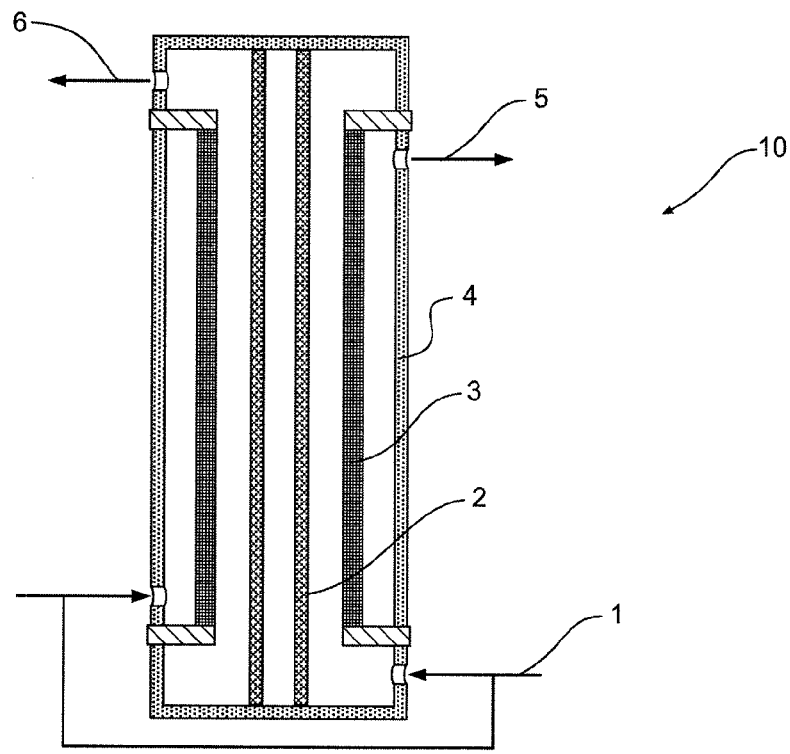
FIG. 1 shows a prior art unipolar activation cell.

FIG. 1 describes a unipolar tubular diaphragm cell patented by Dr. Bakhir et al. The raw water feed 1 is divided into the cathode cell 2 and anode cell 4 that are separated by a ceramic diaphragm 3. The raw water can have mineral content of 0.3 to 1.5 g/l, a Redox potential of from +200 to +400 and contain the chemicals Na; K; Ca; Mg; $SO_4$ and HCO. The anolyte 5 produced is acidic and contains strong biocides such as hydrogen peroxide and ozone. The anolyte has a pH of 0.25 to 7 and a Redox potential of +700 to +1200 mV. It can contain electrolytically synthesized compounds $Cl_2O$; HClO; Cl; $ClO_2$; OH; O; $HO_2$; $H_2O_2$; $O_3$; ClO; $S_2O_8$ and $C_2O_6$. The catholyte 6 produced is alkaline and contains only washing solution. It can have a pH of 7.5 to 13 and a Redox potential of −500 to −800 mV. It can contain electrolytically synthesized compounds NaOH; KOH; HO; $H_2O_2$; $H_3O_2$; $H_2$; and $Ca(OH)_2$. The capacity of this unipolar cell is limited due to the impedance of the diaphragm, and acidic and alkaline waters are produced.

Figure 2:
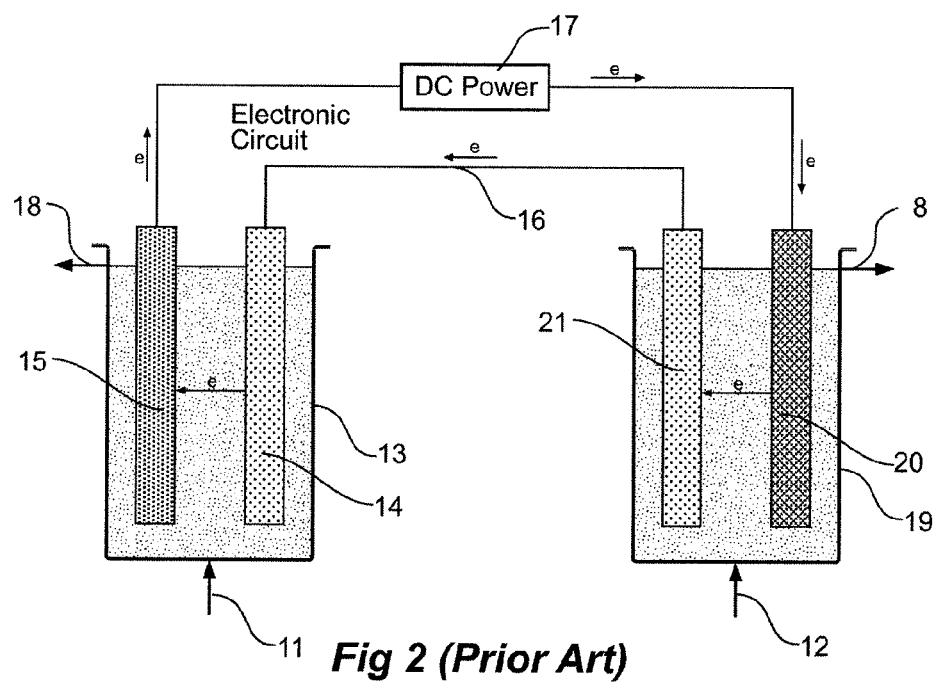
FIG. 2 shows a prior art unipolar diaphragm-less activation system.

FIG. 2 shows the previously patented diaphragm-less unipolar system. Raw water 11 is fed into the anode cell 13 containing the anode electrode 15 and the solution electrode 14. The activated water 18 is discharged from the anode cell 13. Raw water 12 is also fed into the cathode cell 19 containing the cathode electrode 20 and the solution electrode 7. The activated water 8 is discharged from the cathode cell 19. The complete electronic circuit 16 consists of the anode solution electrode 14 through the anolyte 18 to the anode electrode 15 to the DC power source 17 to the cathode electrode 20 though the catholyte 8 to the cathode solution electrode 7 through the external conductor 16 and to the anode solution electrode 14.

DESCRIPTION OF PREFERRED EMBODIMENTS

Figure 3:
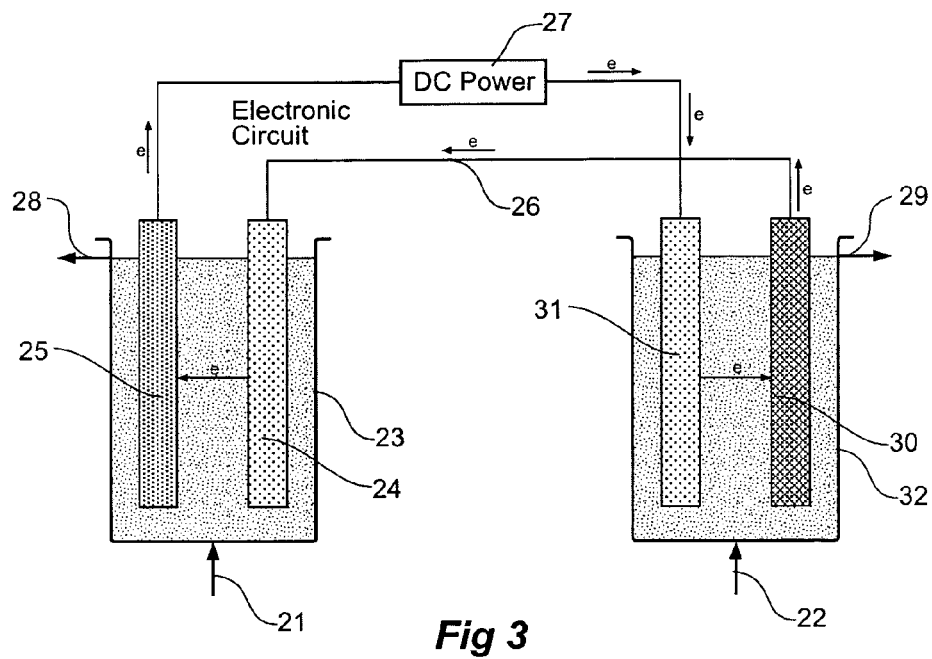
FIG. 3 shows a first embodiment of unipolar activation apparatus according to the present invention in anode mode.

FIG. 3 shows one embodiment of unipolar activation apparatus of the present invention being a unipolar system with the cathode electrode 30 acting as an anode for the maximum production of biocides. The change is achieved mainly by interchanging the connections to the cathode electrode 30 and the cathode solution electrode 31. The flow of electrons is reversed so that electrons are removed from the catholyte 29 by the cathode electrode in the same way that electrons are removed from the anolyte solution 28 by the anode electrode 25.

FIG. 3 shows that raw water 21 is fed into the anode cell 23 containing the anode electrode 25 and the solution electrode 24. The activated water 28 is discharged from the anode cell 23 as an anolyte. Raw water 22 is also fed into the cathode cell 29 containing the cathode electrode 30 and the solution electrode 31. The activated water 29 is discharged from the cathode cell 32.

Figure 3A:
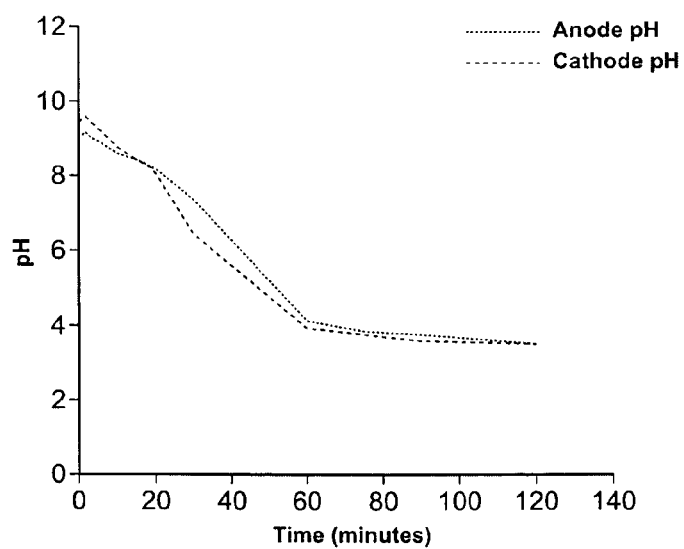
FIG. 3A shows a graph of pH vs time for the operation of the embodiment shown in FIG. 3.

FIG. 3A shows a graph of the pH of the activated anolyte and catholyte waters produced by the arrangement of FIG. 3 and shows that the pH of both anolyte and catholyte are raised initially before falling to below 4.0 after 120 minutes. This is consistent with both the waters producing strong biocides.

Figure 4:
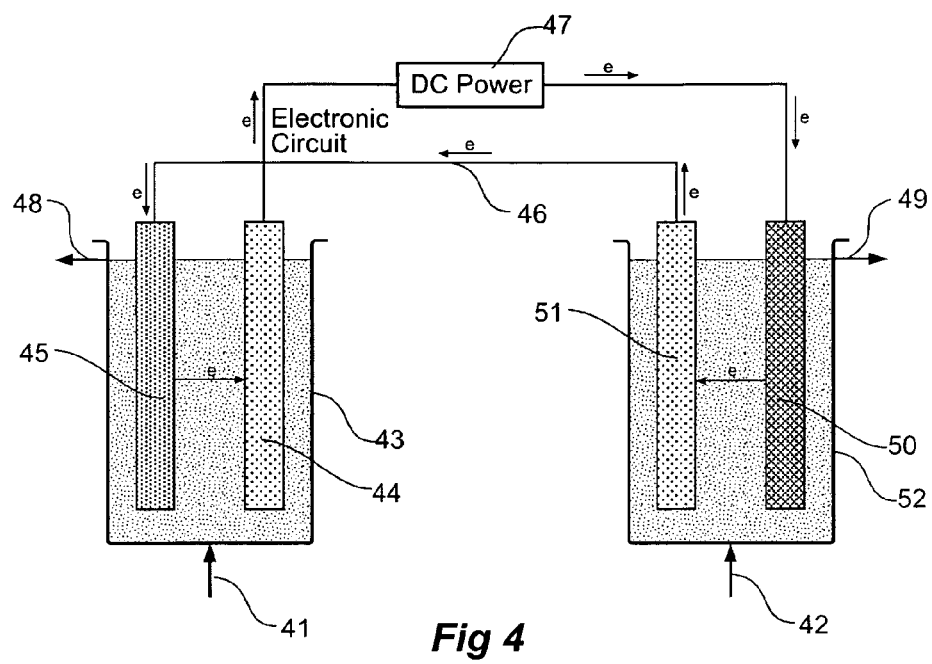
FIG. 4 shows a second embodiment of unipolar activation apparatus according to the present invention in cathode mode.

FIG. 4 shows the unipolar system of the present invention with the anode electrode 45 acting as a cathode electrode. In this cathode mode, both anode electrode 45 and cathode electrode 50 are adding electrons to the anolyte 48 and catholyte 49. In this mode, weak solutions are produced and the coagulating or reducing effect of the unipolar system is maximized.

Figure 4A:
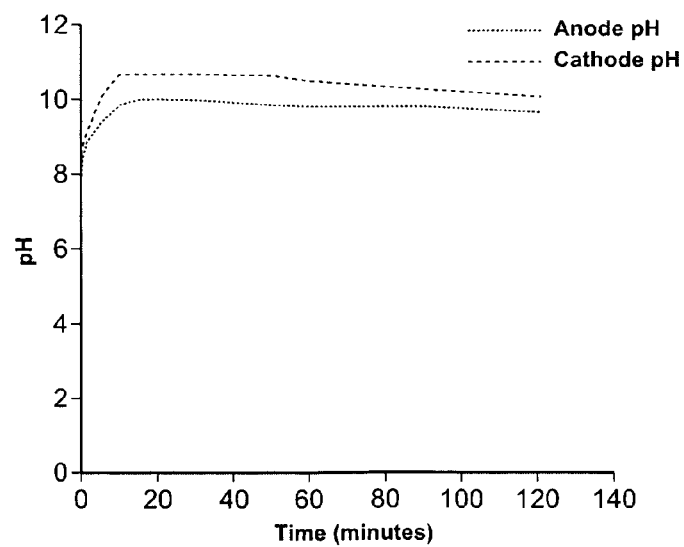
FIG. 4A shows a graph of pH vs time for the operation of the embodiment shown in FIG. 4.

FIG. 4A shows a graph of the pH of the activated anolyte and catholyte waters produced by the arrangement of FIG. 4 and shows that both anolyte 48 and catholyte 49 show an increase of pH over time.

Figure 5:
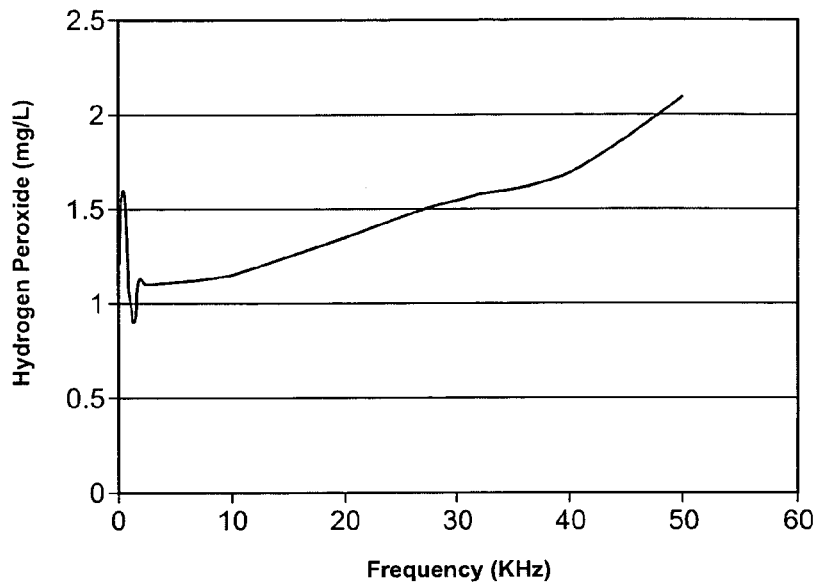
FIG. 5 shows a graph of the pulsing frequency versus the hydrogen peroxide generation for the embodiment shown in FIG. 3.

FIG. 5 shows a graph of pulsing frequency of a DC voltage versus the hydrogen peroxide produced for the embodiment shown in FIG. 3. The graph was taken based on constant voltage and at atmospheric pressure. The graph shows an increase in hydrogen peroxide production as the frequency is increased up to 50 kilohertz.

Figure 6:
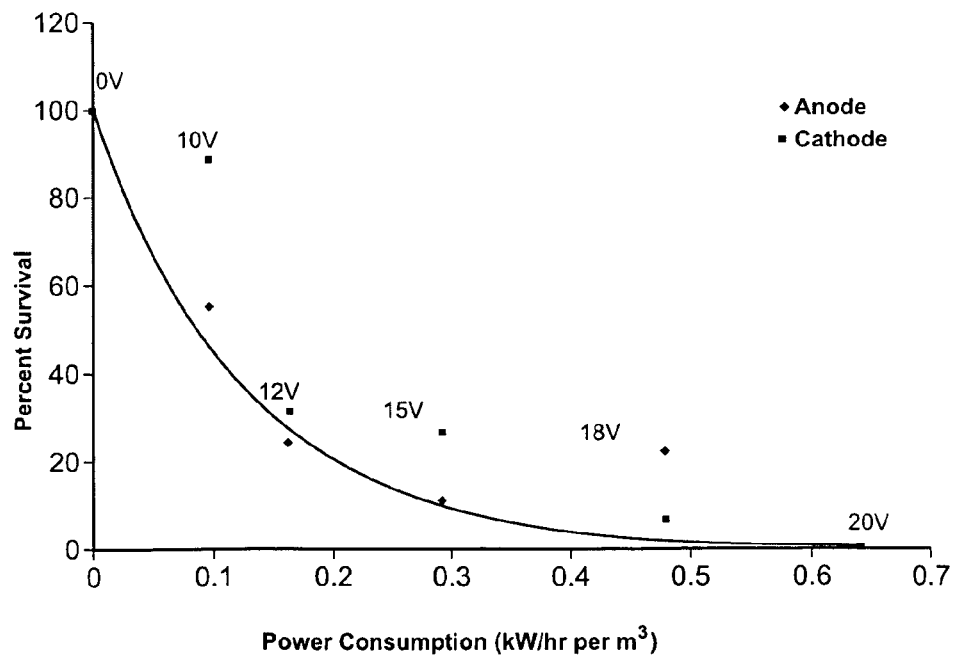
FIG. 6 shows a graph of total pathogen survival rate being the result of treating sewage water with a unipolar activation unit according to the present invention.

FIG. 6 shows one of the results of treating the sewage water with a unipolar activation unit according to the present invention. The unit comprised a portable 200 liters per minute sewage water disinfection unit. A first trailer contained a 14 kw gasoline generator, DC power source and voltage modulators while the pumps, pump box and electrolytic cells were contained in a second trailer. Each cell contained five titanium electrodes 100×1000 mm and six 316 stainless steel 100× 1000 mm solution electrodes. The data in the graph includes both the anolyte and the catholyte. It is estimated the retention time of the sewage water in the unipolar cells is about 30 seconds. It was observed that a brown precipitate formed in the activated water and settled to the bottom of the container. There was also some frothy material at the surface of the activated water but this eventually settled to the bottom when the froth broke down.

Figure 7:
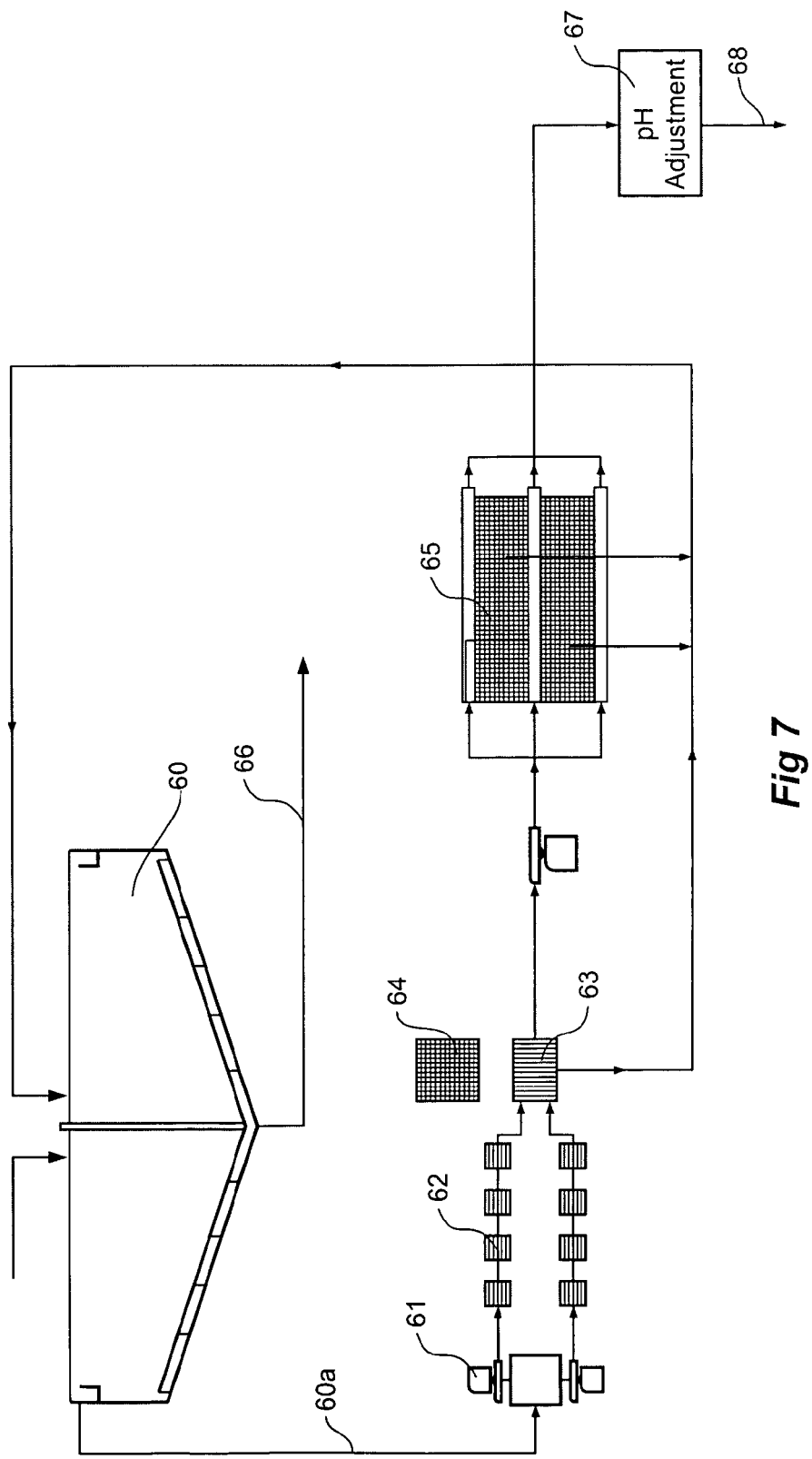
FIG. 7 shows a sewage water disinfection process using a unipolar activation apparatus according to the present invention.

FIG. 7 shows a schematic diagram showing the disinfection of sewage water after aeration at a sewage plant to produce potable water. Feed water 60a is taken from the clarified overflow of a clarifier 60 and pumped by pumps 61 to unipolar cells 62 operating in anode mode. The unipolar activation of the sewage results in coagulation and precipitation of solids, disinfection, and breaking down of pharmaceuticals from the strong biocides such as hydrogen peroxide and ozone. The solids and coagulated molecules are removed by centrifugal separation 63 or by ultra-fine filters 64 with the filtrate passed through an RO filter 65 with the backwash containing dead pathogens recycled to the clarifier 60. pH is adjusted by 67 resulting in the final potable water 68 that is free of pharmaceuticals.

Figure 8:
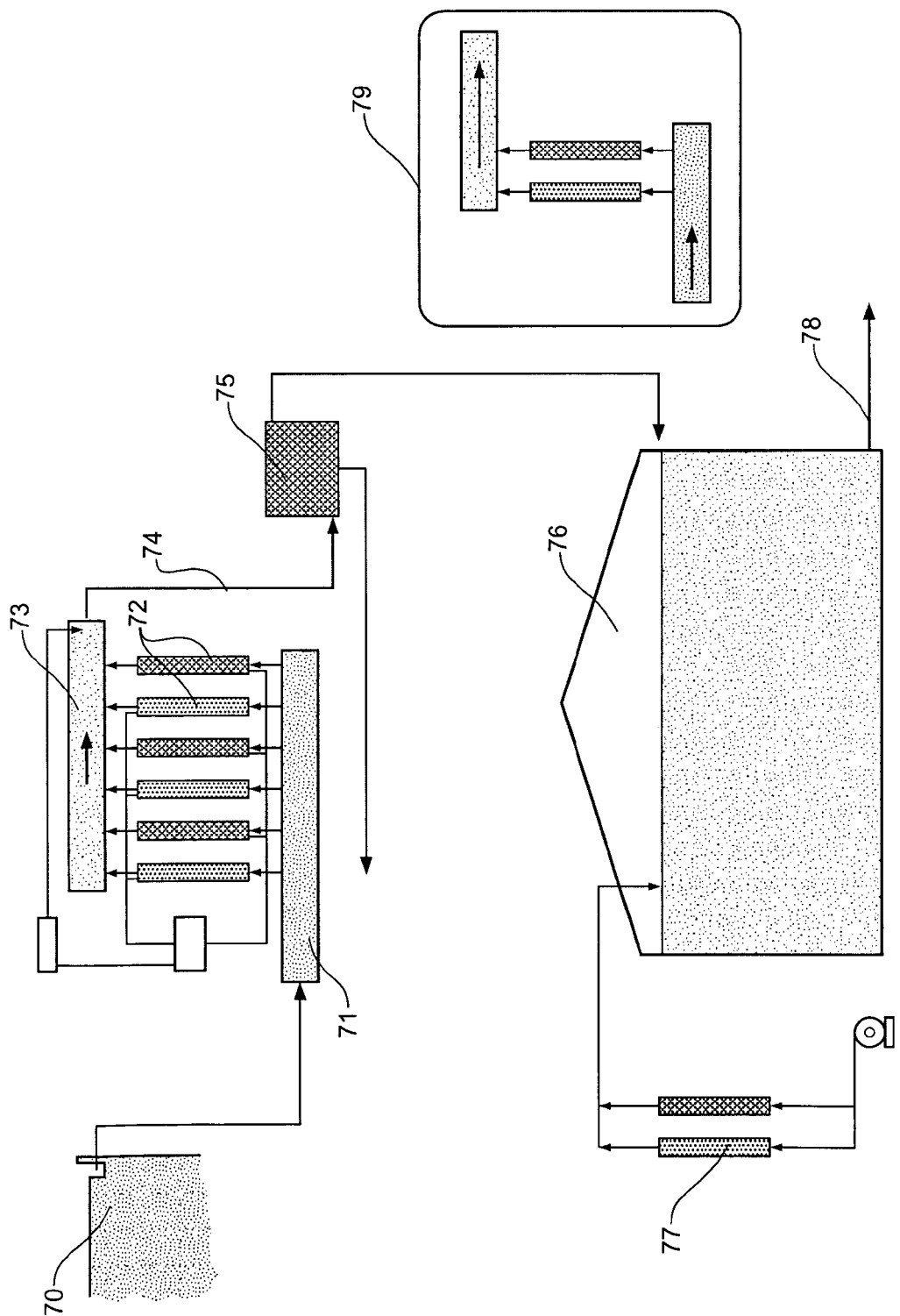
FIG. 8 shows a commercial water disinfection process of a raw water supply using a unipolar activation apparatus according to the present invention.

FIG. 8 shows a schematic diagram showing unipolar disinfection of a raw water supply 70 that is passed through a header 71 through unipolar cells 72 operating on anode mode into a product header 73. The disinfected water 74 is passed through a sand-carbon filter 75 before being placed in a sealed container 76. The sealed container 76 is important to maintain the ozone and hydrogen peroxide in the disinfected water as well as a small unipolar unit 77 treating a circulating stream. The disinfected water 78 without the use of chlorine is delivered to the consumers. Automated biocide top-up units 79 using unipolar activation according to the present invention may be used in remote areas to ensure disinfection of the water.

Figure 9:
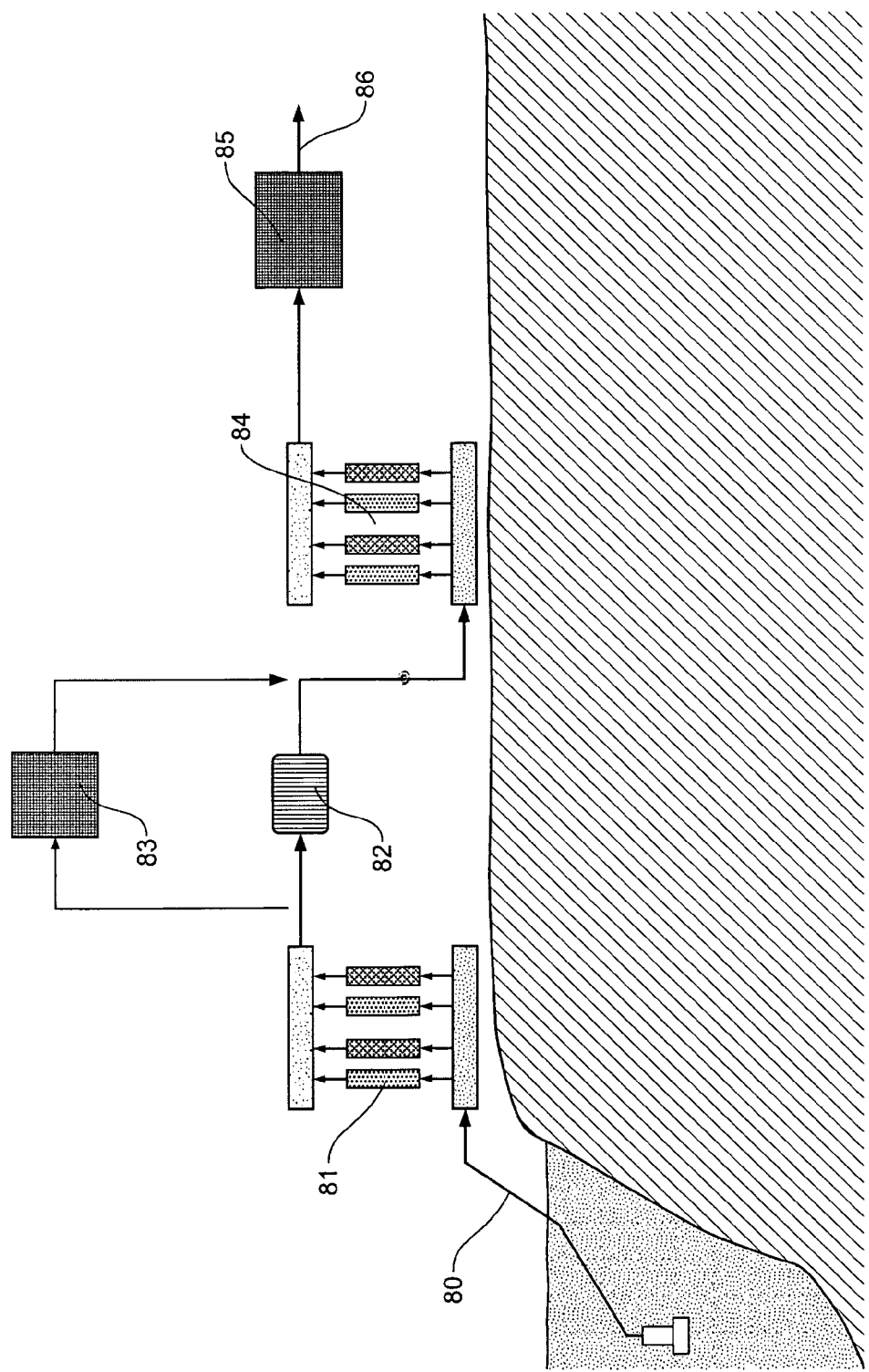
FIG. 9 shows an apparatus for the desalination of seawater utilizing a unipolar activation apparatus according to the present invention.

FIG. 9 shows the use of unipolar activation in agglomerating chemical species in seawater for improved reverse osmosis (RO) desalination to reduce power cost and RO media cost. Seawater 80 is pumped through the unipolar cells 81 and the agglomerated compounds are removed by a high intensity centrifuge 82 or an ultra-fine filter 83. The seawater is then passed through a second stage of coagulation 84 and the product is passed through the RO filters 85 to remove coagulated or decomposed molecules including pharmaceuticals. The final water product 86 may be suitable as potable water or as process water. Coagulation in the seawater occurs due to formation of alkali metal precipitates resulting in less salt to be removed during the RO stage.

The estimated power consumption at each stage is as follows:

| | |
|---|---|
| First unipolar stage | 0.6 kwh/$m^3$ |
| High intensity centrifuge stage | 0.8 kwh/$m^3$ |
| Second unipolar stage | 0.6 kwh/$m^3$ |
| RO stage | 0.8 kwh/$m^3$ |

It is projected that the total power consumption will be about 2.4 to 2.8 kilowatt-hours per cubic meter instead of 4 to 5 kilowatt-hours for conventional RO filtration.

Straight desalination of seawater results in the following disadvantages:

Higher cost of power of 4 to 5 kwh/$m^3$

Higher filter media cost and more frequent replacement

Figure 10:
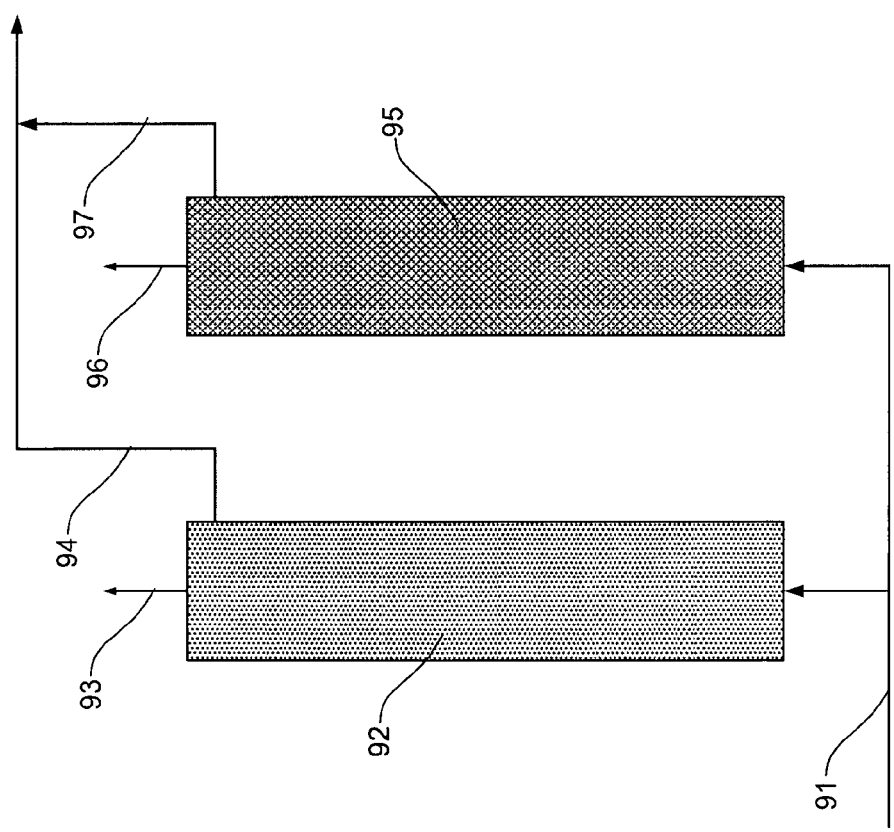
FIG. 10 shows a process for activation of seawater using a unipolar activation apparatus according to the present invention to produce hydrogen.

FIG. 10 shows unipolar activation applied to the production of hydrogen from seawater resulting in excess hydroxyl ions in the activated seawater. In the seawater, there are H(+) and OH(−) ions and when subjected to cathode mode unipolar electrolysis, the hydrogen ion is reduced to hydrogen gas, leaving excess of OH(−) ions. These ions react with elements in the seawater such as sodium, calcium, potassium, and magnesium to form hydroxides. In FIG. 10, seawater 91 is fed to the anode 92 and cathode 95 cells with the anode cell 92 in cathode mode.

Hydrogen 93 and 96 are produced from the anode 92 and cathode 95 cells. Activated seawater 94 and 97 is produced containing sodium, potassium, calcium, and magnesium hydroxides.

Figure 11:
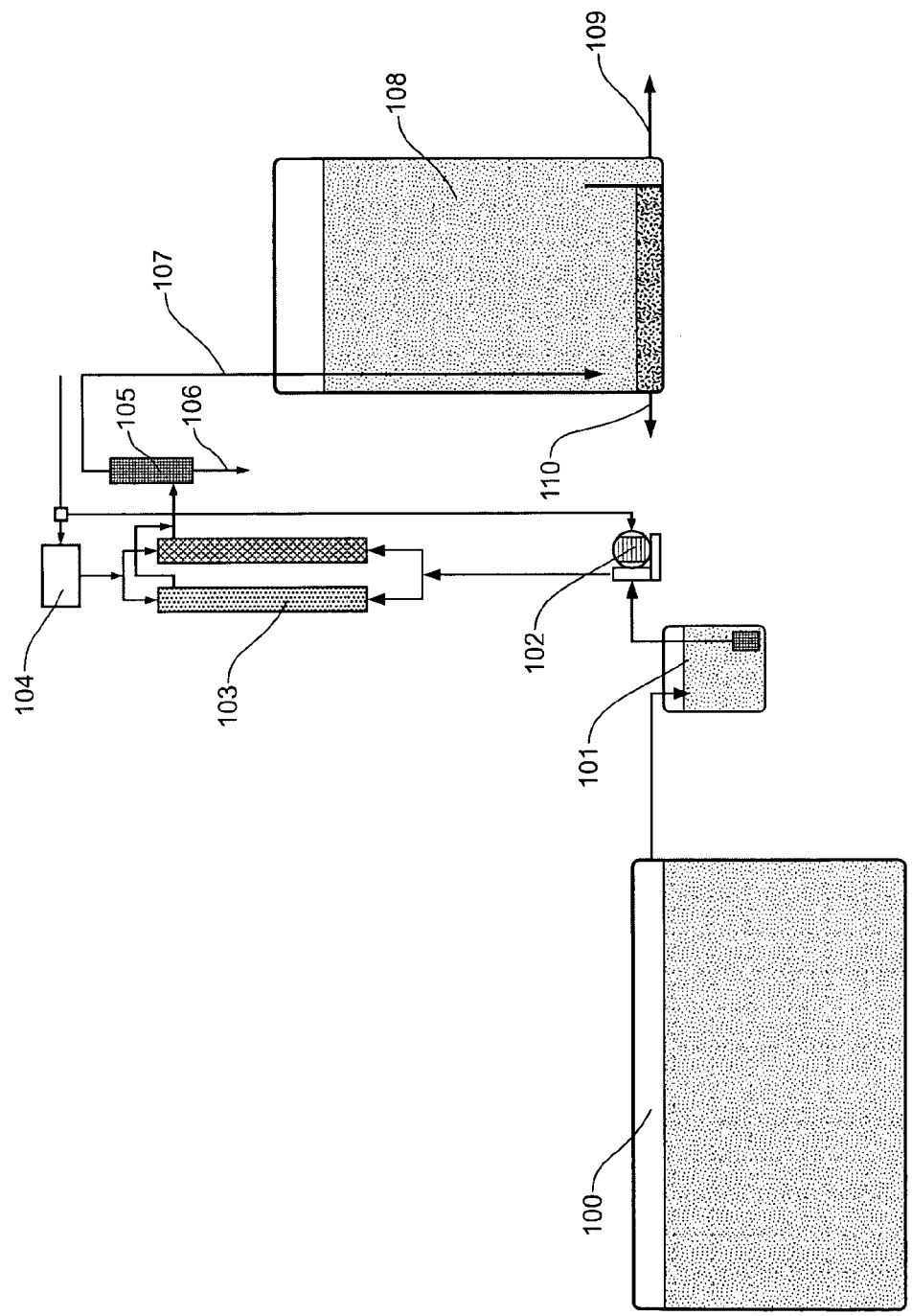
FIG. 11 shows a domestic septic system disinfection process using a unipolar activation apparatus according to the present invention.

FIG. 11 is a diagram showing the application of unipolar disinfection to grey or sewage water in a dwelling. The sewage is processed in a conventional sewage tank 100. The sewage water is collected in a small underground tank 101 where it is pumped 102 through unipolar cells 103 with DC power source 104. The disinfected water is passed through a filter 105 with the clear water 107 stored in the storage tank 108 where irrigation quality water 109 is available for use. The filter backwash 106 is returned to the septic tank.

Figure 12:
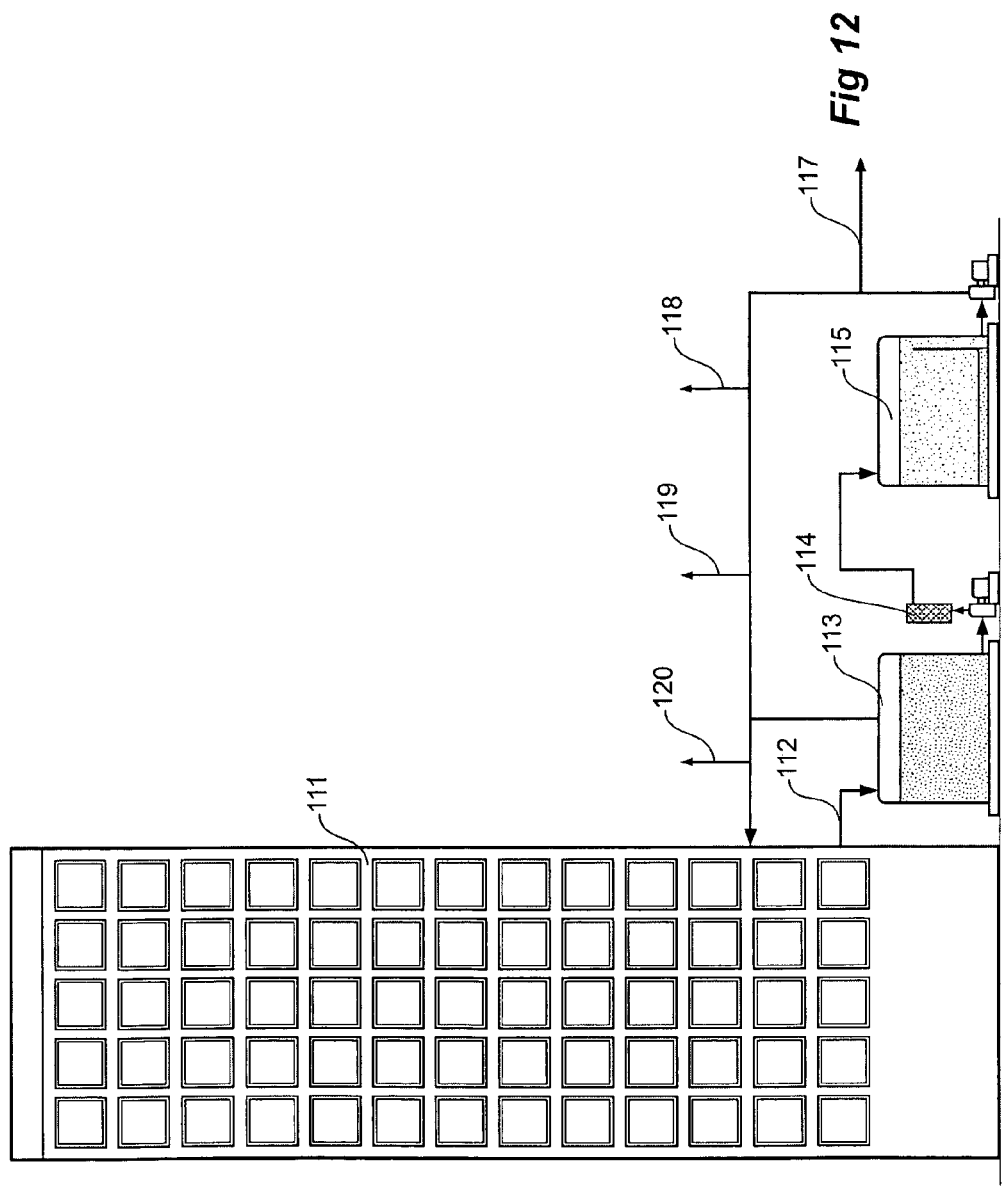
FIG. 12 shows a grey water disinfection process using a unipolar activation apparatus according to the present invention for high rise buildings.

FIG. 12 is a diagram showing unipolar activation applied to disinfection of grey water in a high rise building for recycling. Grey water 112 is collected in a storage tank 113 and then passed through unipolar cells 114 before storage in the Class A water tank 115 where the disinfected water 117 is used for irrigation or laundry 119 and toilets 120. The system is also applicable to a small community instead of a high rise building.

Figure 13:
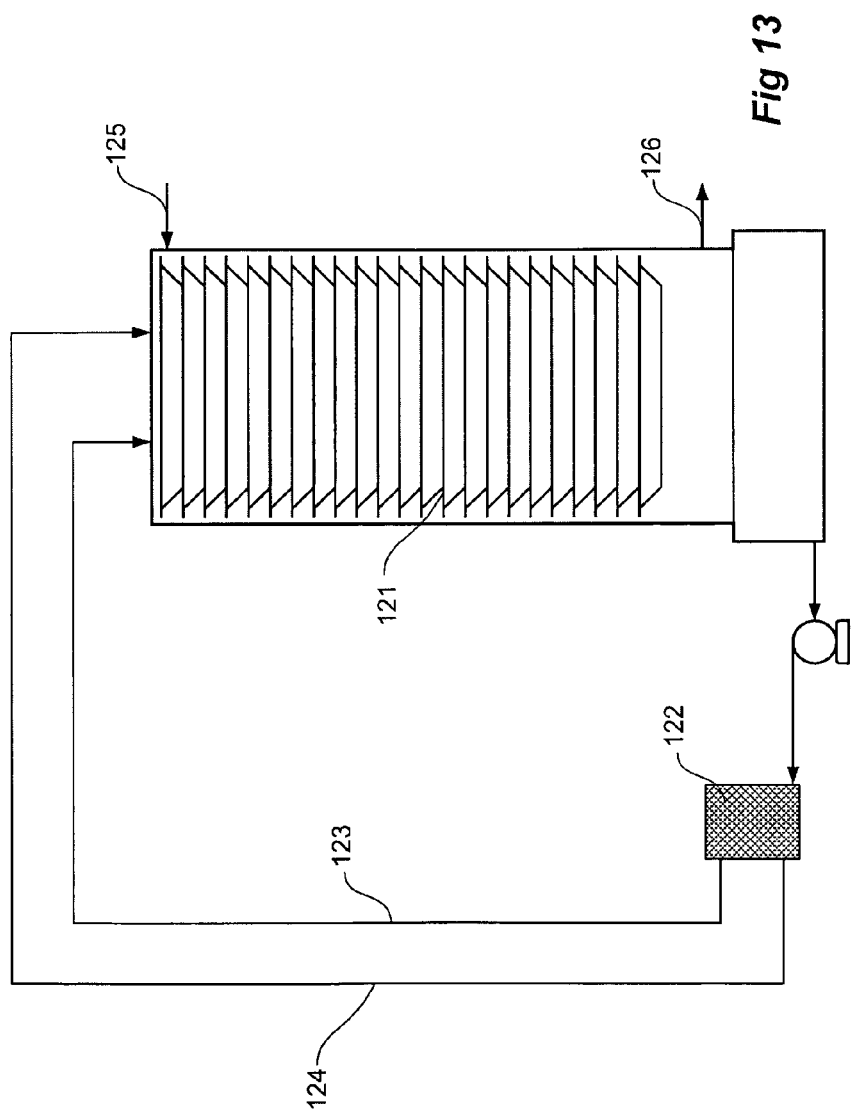
FIG. 13 shows a process for unipolar activation of a cooling tower for the control of legionella according to the present invention.

FIG. 13 shows unipolar activation applied to a cooling tower to control legionella. Water with about 3 grams per liter of salt from the cooling tower 121 is passed through unipolar cells 122 in anode mode with the anolyte 123 and catholyte 124 sprayed at the top of the cooling tower. The biocides produced include strong chloride biocides, hydrogen peroxide and ozone which are sufficient to kill pathogens including legionella that the activated water comes in contact with. The unipolar cells could be pressurized to produce more hydrogen peroxide and ozone and less salt in the water used so that less chloride biocides are produced if these are harmful to the application such as cooling tower systems used in art galleries.

Figure 14:
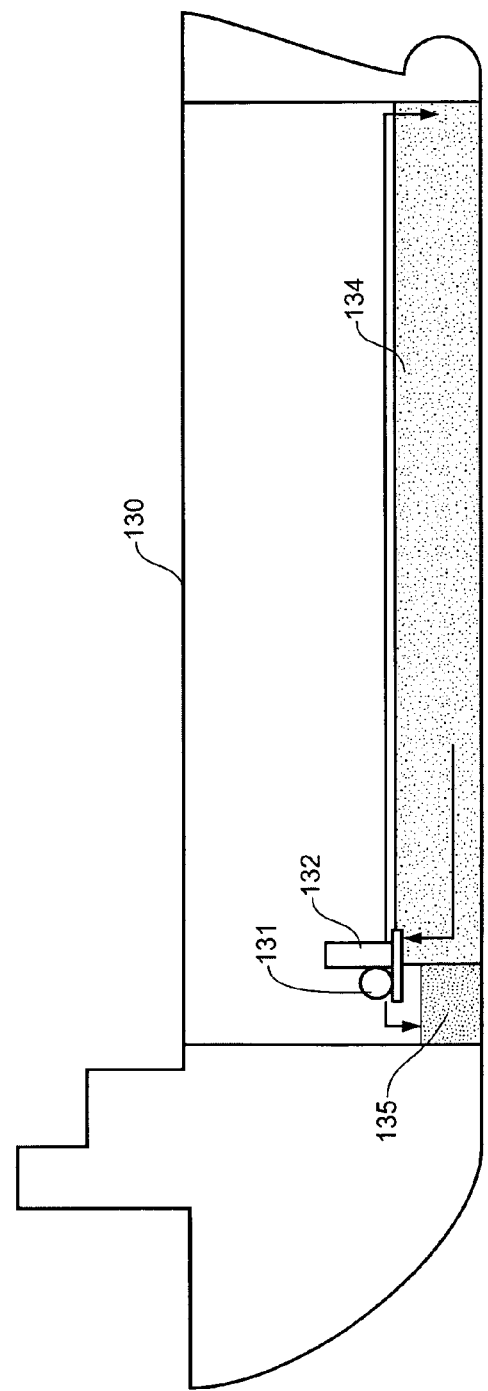
FIG. 14 shows unipolar activation to disinfect ballast water according to the present invention.

FIG. 14 shows unipolar activation to disinfect ballast water. This is a relatively simple procedure because unladen ships normally take on seawater for ballast during their journey to the next port. Harmful organisms can be brought from one port to the next port. The unipolar cells 132 are installed in the hold of ship 130 and the ballast water 133 is activated as well as passed through a liquid vortex separator 131 to remove the oil from the ballast water 134. The activated water kills all organisms in the ballast water so that the ballast water can safely be discharged at the port of call without introducing harmful organisms.

Figure 15:
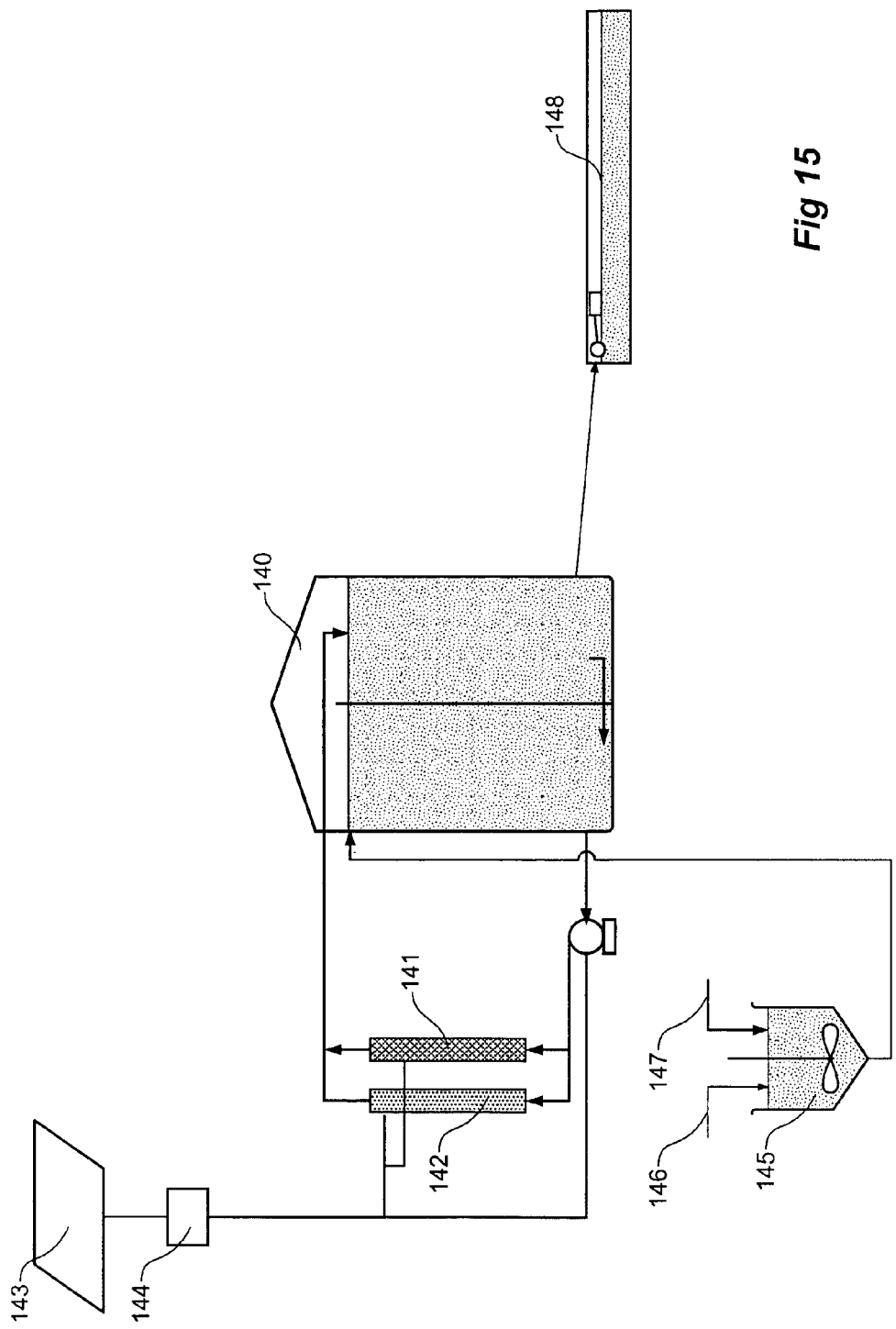
FIG. 15 shows a process for unipolar activation of water for poultry and farm animals according to the present invention.

FIG. 15 shows activation of water for poultry and farm animals. The objective of this process is threefold: (1) to reduce the emission of methane gas from these animals (2) to convert the methane to weight gain and (3) to strengthen the immune system of the animals from infectious diseases. Raw water 147 for watering the animals may be fed into a mixing tank 145 where additives 146 that will help the health or growth of the animals is mixed before the mixture is transferred to a storage tank 140 before being fed to unipolar cells 141 and 142 that are powered by any of several power sources 143 with or without a battery backup 144. The activated water is stored and then used as required to water the farm animals or poultry in a trough 148.

Figure 16:
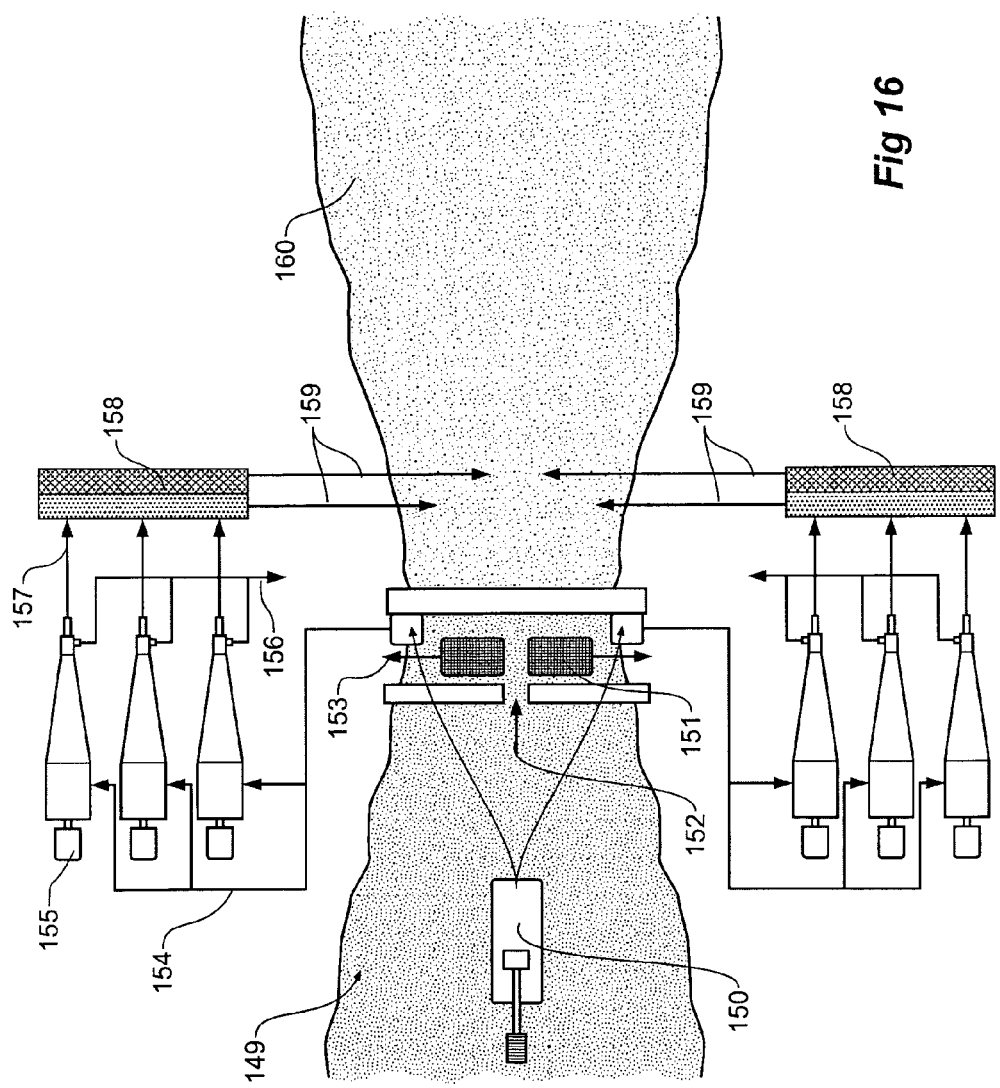
FIG. 16 shows a process for disinfection of polluted rivers according to the present invention.

FIG. 16 is a diagram of unipolar activation in purifying a polluted river or waterway. Polluted rivers result from human waste or from industrial waste. The polluted river 149 is dammed at an appropriate location and floating trash is directed to several rotary screens 151, 152 fitted with spirals that transfer the solid trash 153 to shore where it is burned or used as land fill. The polluted river water 154 is fed to several liquid vortex separators 155 where a major fraction 157 containing small amount fine solids is passed through unipolar cells 158 where disinfection and coagulation is achieved and this liquid 159 is returned to the clean side of the river 160. Some of the pollution settles at the bottom of the river and this material is dredged 150 and sent to the pump box of the liquid vortex separators 155. The high solids stream 156 from the liquid vortex separators 155 is sent to land fill. This treatment procedure for the river may be repeated several times along a polluted river.

Figure 17:
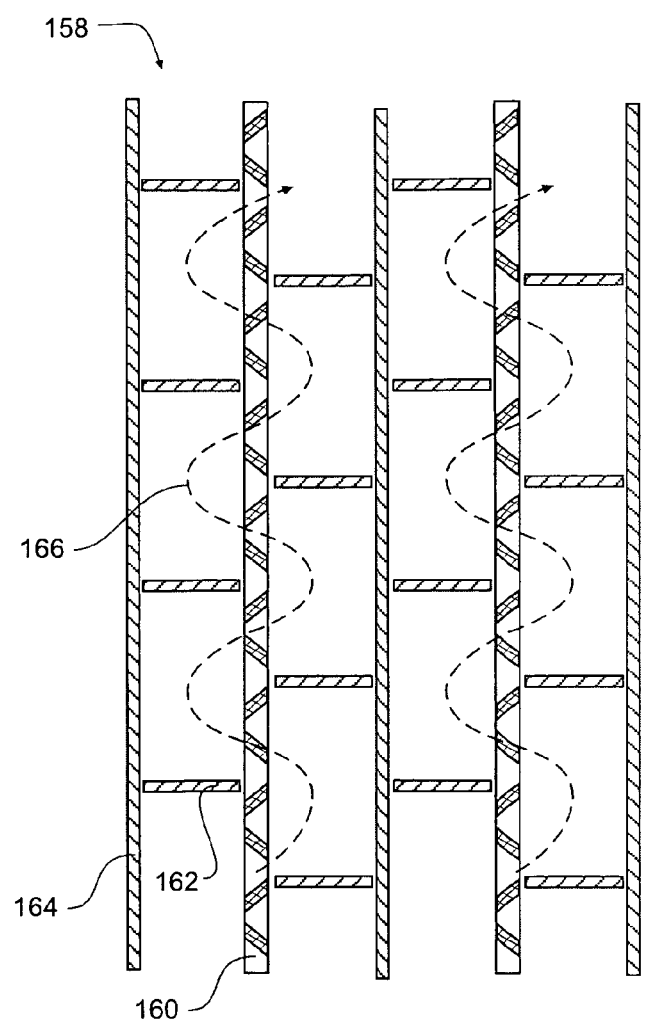
FIG. 17 shows detail of the construction of the electrodes according to a preferred embodiment of the invention.

FIG. 17 shows detail of the construction of the electrodes according to a preferred embodiment of the invention. In this embodiment, which is applicable to both the anode cell assembly and the cathode cell assembly 158, the electrode (cathode or anode) 160 is formed from an expanded metal sheet to give it a large surface area, active sites and to encourage turbulent flow over the surface of the electrode. The electrode may be formed from iron, aluminum or stainless steel (316 stainless steel) with or without a coating to prevent corrosion and to providing a low over-voltage. Alternatively the electrode may be titanium coated with platinum group oxides. Around the electrode 150 is a baffle arrangement 162. The baffle arrangement 162 is formed from an electrically non-conductive material and is placed to force the water to weave in and out of the expanded metal electrode. Surrounding the baffle arrangement are sheet metal solution electrodes 164. The solution electrodes may be constructed from titanium coated with platinum group oxides or stainless steel (316 stainless steel). Water flow through the electrode assembly is shown by the dotted line 166. It will be seen that the water follows a tortuous path thereby encouraging good contact with the respective electrode.

Discussion

1. The most important feature of this invention is the ability to make the cathode cell behave like an anode cell and conversely, the anode cell behave like the cathode cell. It is an invention that many well versed with the conventional diaphragm cell find difficult to believe. With our diaphragm-less electrolytic cell, the science can easily be demonstrated and the invention has been demonstrated in a substantial number of small and large experiments. This embodiment of our invention can be applied to a number of important chemical processes that have major impact on water disinfection and on the environment.

For water purification, strong biocides are produced at the anode cell and by connecting the cathode so that it behaves like an anode cell, the energy is productively used to produce strong biocides such as hydrogen peroxide and ozone.

If the anode is connected so that is behaves like a cathode, reducing reactions occur at both cells and a major application is in the activation of seawater to extract and sequester carbon dioxide from a power plant flue gas stream or from the air. In the seawater which is a dilute solution of halite, the H(+) and OH(−) ions exist in the water along with ions of Na(+), K(+), Ca(++), and Mg(++). When the seawater is passed through the unipolar cells in cathode mode, electrons are removed from the seawater and the following reaction occurs:

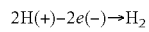

$$2H(+) - 2e(-) \rightarrow H_2$$

This leaves an excess of OH(−) ions in the seawater resulting in the formation of the hydroxides of Na, K, Ca, and Mg. When this activated seawater is contacted with carbon dioxide gas, the $CO_2$ is absorbed and reacts with the water as follows:

$$CO_2 + H_2O \rightarrow H_2CO_3$$

The carbonic acid reacts with the base Na, K, Ca, and Mg hydroxides to form carbonates of Na, K, Ca, and Mg. One objective in manipulating this system is to try to produce bicarbonates as twice the amount of carbon dioxide is sequestered theoretically by the Na, K, Ca, and Mg contained in the seawater. Modifiers can be added to the seawater before or after activation to increase the absorption of carbon dioxide into the activated seawater. Seawater has been selected as a means of sequestering carbon dioxide as the oceans of the world have a capability to absorb up to 200,000 gigatonnes of carbon dioxide. Waters which have a high content of alkali metals would also be suitable for activation to absorb carbon dioxide. Absorption of the carbon dioxide can be carried out at elevated pressure and temperature to achieve more efficient absorption and sequestration of the carbon dioxide. Having excess carbon dioxide, preferably carried out in a counter-current absorption system, will encourage the production of alkali bicarbonates allowing more sequestration of carbon dioxide for the same amount of alkali metals in the original water.

2. Pulsing current is a major feature of this invention as it was shown experimentally that very little reaction happens if the current is not pulsing. The experiments indicated that maximum reaction occurs at 50 kilohertz but it is expected that higher frequency will increase the reaction but will reach a peak as the pulsing frequency is increased.

3. The duty cycle of the pulsing current found to give the best results is about 60 percent but this is not a definite conclusion and it is considered that a duty cycle of 40 to 60% would be adequate for most applications.

4. During disinfection, a higher pressure even in small increment resulted in higher production of hydrogen peroxide and ozone. The addition of oxygen during unipolar activation did not seem to increase the amount of biocide production so that it is difficult to put forward an explanation for the increased biocide production with a small increment in pressure.

5. The unipolar electrolytic process of this invention can produce acidic water with strong biocides when the cathode is acting as an anode or alkaline water when the anode is acting as a cathode. There are many who believe that alkaline water is good for human and animal health.

The invention claimed is:

1. A unipolar electrolytic apparatus to activate separate streams of raw water, the apparatus comprising;
   an anode cell assembly and a cathode cell assembly,
   the anode cell assembly including an anode electrode and an anode cell solution electrode, a raw water inlet and a treated anolyte outlet;
   the cathode cell assembly including a cathode electrode and a cathode cell solution electrode, a raw water inlet and a treated catholyte outlet;
   a power supply that provides a DC pulsed current to the anode cell assembly and the cathode cell assembly,
   the anode electrode comprising an expanded metal mesh and comprising or being coated with a material providing a low over-voltage and resistance to corrosion, a baffle surrounding the anode electrode, the baffle comprising an electrically non-conductive material to force the water to weave in and out of the expanded metal electrode, the anode cell solution electrode comprising a sheet metal and the anode cell solution electrode surrounding the baffle; and
   the cathode electrode comprising an expanded metal mesh and comprising or being coated with a material providing a low over-voltage and resistance to corrosion, a baffle surrounding the cathode electrode, the baffle comprising an electrically non-conductive material to force the water to weave in and out of the expanded metal electrode, the cathode cell solution electrode comprising a sheet metal and the cathode cell solution electrode surrounding the baffle;
   a raw water supply to each of the anode cell and the cathode cell, a treated anolyte take off line from the anode cell and a treated catholyte take off line from the cathode cell,
   the electrical connections of the cathode solution electrode and the cathode electrode being interchanged to result in the cathode cell behaving like an anode cell in an anode mode, or the electrical connections between the anode solution electrode and the anode electrode being interchanged to result in the anode cell behaving like the cathode cell in a cathode mode, whereby oxidizing reactions occur in the water at both anode cell and cathode cell in the anode mode, such that strong biocides are produced in both the anode cell and the cathode cell, and where reducing reactions occur in the water at both anode cell and cathode cell in the cathode mode, whereby to produce the treated anolyte from the anode cell and the treated catholyte from the cathode cell.

2. A unipolar electrolytic apparatus as in claim 1 wherein the DC current applied has a pulse frequency of 20 to 200 kilohertz.

3. A unipolar electrolytic apparatus as in claim 1 wherein the DC pulsing current has a duty cycle of the range of from 20 to 80 percent.

4. A unipolar electrolytic apparatus as in claim 1 wherein the anode cell assembly and the cathode cell assembly operates at a temperature of from 10 degrees Celsius to 200 degrees Celsius.

5. A unipolar electrolytic apparatus as in claim 1 wherein the anode and cathode cell assembly operate at a pressure of from atmospheric pressure up to 300 psig (22 atm).

6. A unipolar electrolytic apparatus as in claim 1 wherein the anode cell and cathode cell solution electrodes are of solid construction to guide the water to weave in and out of the expanded metal electrode.

* * * * *